US00RE46179E

(19) United States
(12) Reissued Patent
Hart

(10) Patent Number: US RE46,179 E
(45) Date of Reissued Patent: Oct. 18, 2016

(54) ROTATION KNOBS FOR SURGICAL INSTRUMENTS

(71) Applicant: Covidien LP, New Haven, CT (US)

(72) Inventor: Keir Hart, Lafayette, CO (US)

(73) Assignee: COVIDIEN LP, New Haven, MA (US)

(21) Appl. No.: 14/748,809

(22) Filed: Jun. 24, 2015

Related U.S. Patent Documents

Reissue of:
(64) Patent No.: 8,679,098
Issued: Mar. 25, 2014
Appl. No.: 13/231,643
Filed: Sep. 13, 2011

(51) Int. Cl.
*A61B 17/00* (2006.01)
*A61B 18/14* (2006.01)

(52) U.S. Cl.
CPC ..... *A61B 18/14* (2013.01)

(58) Field of Classification Search
CPC ..... A61B 19/22; A61B 19/2203
USPC ..... 606/1, 169; 604/22, 45
See application file for complete search history.

(56) References Cited

U.S. PATENT DOCUMENTS

| | | | |
|---|---|---|---|
| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| D343,453 | S | 1/1994 | Noda |
| D348,930 | S | 7/1994 | Olson |
| D349,341 | S | 8/1994 | Lichtman et al. |
| D354,564 | S | 1/1995 | Medema |
| D358,887 | S | 5/1995 | Feinberg |
| D384,413 | S | 9/1997 | Zlock et al. |
| H1745 | H | 8/1998 | Paraschac |
| D402,028 | S | 12/1998 | Grimm et al. |
| D408,018 | S | 4/1999 | McNaughton |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Beverly M Flanagan

(57) ABSTRACT

A surgical instrument includes a housing having a shaft extending therefrom. The housing includes a nose having a neck and a base that defines a diameter greater than that of the neck. A rotation knob has a distal end defining a first aperture and a proximal end defining a second aperture, the apertures cooperating to define a lumen extending through the rotation knob that is configured to receive the shaft. The first aperture defines a diameter that generally approximates a diameter of the shaft. The rotation knob is transitionable between an at-rest position and a flexed position. In the flexed position, the second aperture is expanded to permit passage of the base of the nose into an interior of the rotation knob. In the at-rest position, the second aperture generally approximates the diameter of the neck to rotatably engage the rotation knob about the nose with the shaft extending therethrough.

18 Claims, 8 Drawing Sheets

(56) References Cited

U.S. PATENT DOCUMENTS

| | | | | |
|---|---|---|---|---|
| D416,089 | S | | 11/1999 | Barton et al. |
| 5,993,470 | A | * | 11/1999 | Yoon ..... A61B 17/3496 604/165.02 |
| D424,694 | S | | 5/2000 | Tetzlaff et al. |
| D425,201 | S | | 5/2000 | Tetzlaff et al. |
| 6,063,050 | A | * | 5/2000 | Manna et al. . A61B 17/320092 601/2 |
| H1904 | H | | 10/2000 | Yates et al. |
| D449,886 | S | | 10/2001 | Tetzlaff et al. |
| D453,923 | S | | 2/2002 | Olson |
| D454,951 | S | | 3/2002 | Bon |
| D457,958 | S | | 5/2002 | Dycus et al. |
| D457,959 | S | | 5/2002 | Tetzlaff et al. |
| H2037 | H | | 7/2002 | Yates et al. |
| D465,281 | S | | 11/2002 | Lang |
| D466,209 | S | | 11/2002 | Bon |
| D493,888 | S | | 8/2004 | Reschke |
| D496,997 | S | | 10/2004 | Dycus et al. |
| D499,181 | S | | 11/2004 | Dycus et al. |
| D502,994 | S | | 3/2005 | Blake, III |
| D509,297 | S | | 9/2005 | Wells |
| D525,361 | S | | 7/2006 | Hushka |
| D531,311 | S | | 10/2006 | Guerra et al. |
| D533,274 | S | | 12/2006 | Visconti et al. |
| D533,942 | S | | 12/2006 | Kerr et al. |
| D535,027 | S | | 1/2007 | James et al. |
| D538,932 | S | | 3/2007 | Malik |
| D541,418 | S | | 4/2007 | Schechter et al. |
| D541,611 | S | | 5/2007 | Aglassinger |
| D541,938 | S | | 5/2007 | Kerr et al |
| D545,432 | S | | 6/2007 | Watanabe |
| D547,154 | S | | 7/2007 | Lee |
| D564,662 | S | | 3/2008 | Moses et al. |
| D567,943 | S | | 4/2008 | Moses et al. |
| D575,395 | S | | 8/2008 | Hushka |
| D575,401 | S | | 8/2008 | Hixson et al. |
| D582,038 | S | | 12/2008 | Swoyer et al. |
| D617,900 | S | | 6/2010 | Kingsley et al. |
| D617,901 | S | | 6/2010 | Unger et al. |
| D617,902 | S | | 6/2010 | Twomey et al. |
| D617,903 | S | | 6/2010 | Unger et al. |
| D618,798 | S | | 6/2010 | Olson et al. |
| D621,503 | S | | 8/2010 | Otten et al. |
| D627,462 | S | | 11/2010 | Kingsley |
| D628,289 | S | | 11/2010 | Romero |
| D628,290 | S | | 11/2010 | Romero |
| 7,842,028 | B2 | | 11/2010 | Lee |
| D630,324 | S | | 1/2011 | Reschke |
| 2006/0079875 | A1 | | 4/2006 | Faller et al. |
| 2009/0105750 | A1 | | 4/2009 | Price et al. |
| 2010/0193566 | A1 | | 8/2010 | Scheib et al. |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/328,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.

(56) References Cited

OTHER PUBLICATIONS

U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson
U.S. Appl. No. 12/877,199, filed Sep. 8, 2010, Arlen J. Reschke.
U.S. Appl. No. 12/877,482, filed Sep. 8, 2010, Gary M. Couture
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

(56) References Cited

OTHER PUBLICATIONS

Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" Miccai 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.

(56) References Cited

OTHER PUBLICATIONS

Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

ROTATION KNOBS FOR SURGICAL INSTRUMENTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND

1. Technical Field

The present disclosure relates to surgical instruments and, more particularly, to rotation knobs for surgical instruments having rotatable end effector assemblies.

2. Background of Related Art

As an alternative to open surgical instruments for use in open surgical procedures, many modern surgeons use endoscopic apparatus for remotely accessing tissue through smaller openings or incisions. As a direct result thereof, patients tend to benefit from less scarring, fewer infections, shorter hospital stays, less pain, less restriction of activity, and reduced healing time. A typical endoscopic instrument includes a housing, an end effector assembly, and a shaft interconnecting the housing and the end effector assembly. The housing includes one or more controls that are operable to control the end effector assembly such that the end effector assembly may be inserted through the opening in tissue and into the internal surgical site, while the housing remains externally disposed, allowing the surgeon to manipulate the housing controls to control operation of the end effector assembly within the internal surgical site.

An endoscopic surgical forceps, for example, includes a plier-like end effector assembly which relies on mechanical action between its jaw members to grasp, clamp and constrict vessels or tissue. Energy-based surgical forceps utilize both mechanical clamping action and energy, e.g., electrical energy, ultrasonic energy, light energy, thermal energy, etc., to treat tissue. In some procedures, once the tissue has been treated, the surgeon has to sever the tissue and, as such, many forceps have been designed which incorporate a knife or blade member that effectively severs the tissue after treating the tissue.

The housings of endoscopic surgical forceps typically include a movable handle for opening and closing the jaw members, a trigger for selectively advancing the knife or blade, and an actuator for controlling the supply of energy to the end effector assembly. Further, some handle assemblies incorporate a rotation assembly that is operable to selectively rotate the end effector assembly in order to position the end effector assembly as desired within the internal surgical site.

SUMMARY

As used herein, the term "distal" refers to the portion that is being described which is further from a user, while the term "proximal" refers to the portion that is being described which is closer to a user.

In accordance with one aspect of the present disclosure, a surgical instrument is provided. The surgical instrument includes a housing having a shaft extending distally therefrom. The shaft defines a longitudinal axis. The housing includes a nose disposed at a distal end thereof. The nose includes a neck extending distally from the housing and a base disposed at a distal end of the neck. The base defines a diameter that is greater than a diameter of the neck. The surgical instrument further includes a rotation knob having a distal end defining a first aperture and a proximal end defining one or more second apertures. The first aperture defines a diameter that generally approximates a diameter of the shaft. The first and second apertures cooperate to define a lumen extending longitudinally through the rotation knob. The lumen is configured to receive the shaft. The rotation knob is transitionable between an at-rest position and a flexed position. In the flexed position, the diameter of the second aperture is expanded to permit passage of the base of the nose through the second aperture and into an interior of the rotation knob. In the at-rest position, the second aperture defines a diameter that generally approximates the diameter of the neck of the nose to rotatably engage the proximal end of the rotation knob about the nose with the shaft extending through the lumen of the rotation knob.

In one aspect, the rotation knob includes one or more protrusions extending into the interior thereof. The protrusion(s) is configured to engage the shaft, e.g., cut-outs defined within the shaft, to engage the rotation knob and the shaft to one another.

In another aspect, the rotation knob includes a retaining ring configured to bias the rotation knob towards the at-rest position. The retaining ring may include an interruption defined therein that permits expansion of the retaining ring to thereby permit transitioning of the rotation knob between the at-rest and flexed positions.

In still another aspect, the rotation knob includes first and second pairs of proximal support walls. Each pair of proximal support walls cooperates to define one of the second apertures therethrough. In this configuration, the retaining ring may be disposed between the first and second pairs of proximal support walls.

In yet another aspect, the rotation knob includes a plurality of alternating flanges and recesses disposed on the outer periphery thereof. The alternating flanges and recesses are configured to facilitate grasping and rotating the rotation knob.

In still yet another aspect, an outer distal corner of the base of the nose defines an angled surface configured to facilitate transitioning of the rotation knob from the at-rest position to the flexed position to permit passage of the base through the one or more second apertures.

In another aspect, the rotation knob is monolithically formed as a single component.

In yet another aspect, the housing is formed from first and second housing parts. In this configuration, when the rotation knob is engaged about the nose of the housing, the rotation knob helps maintain the engagement of the first and second housing parts to one another.

In accordance with the present disclosure, another aspect of a surgical instrument is provided. The surgical instrument includes a housing having a shaft extending distally therefrom. The shaft defines a longitudinal axis. The housing includes a nose disposed at a distal end thereof. The nose includes a neck extending distally from the housing and a base disposed at a distal end of the neck. The base defines a diameter that is greater than a diameter of the neck. The surgical instrument further includes a rotation knob. The rotation knob has a distal end defining a first aperture and a plurality of radially-spaced fingers extending proximally from a proximal end of the rotation knob. The fingers each including a radially inwardly-extending tab disposed at a free end thereof. The tabs cooperate with one another to define a second aperture. The first aperture defines a diameter that generally approximates a diameter of the shaft. The first and second apertures cooperate to define a lumen extending longitudinally through the rotation knob that is configured to receive the shaft. The rotation knob is transitionable between an at-rest position and a flexed position. In the flexed position, the fingers are flexed radially outwardly to expand a diameter of the second aperture to permit passage of the base of the nose through the second aperture and into an interior of the rotation knob. In the at-rest position, the second aperture defines a diameter that generally approximates the diameter of the neck of the nose to rotatably engage the tabs of the fingers of the rotation knob about the nose, with the shaft extending through the lumen of the rotation knob.

In one aspect, the rotation knob includes one or more protrusions extending into the interior thereof. The protrusion(s) is configured to engage the shaft, e.g., a cut-out defined within the shaft, to engage the rotation knob and the shaft to one another.

In one aspect, the fingers are biased towards the at-rest position.

In another aspect, the rotation knob is monolithically formed as a single component.

In yet another aspect, the housing is formed from first and second housing parts. In this configuration, when the rotation knob is engaged about the nose of the housing, the rotation knob helps maintain the engagement of the first and second housing parts to one another.

In accordance with yet another aspect of the present disclosure, a surgical instrument is provided. The surgical instrument includes a housing and a shaft extending distally from the housing. The shaft defines a longitudinal axis and extends through an aperture defined within a distal surface of the housing. The shaft further includes a bushing disposed about the shaft towards a proximal end thereof. The surgical instrument further includes a rotation knob. The rotation knob includes a proximal end, a distal end, and a lumen extending longitudinally therethrough that is configured to receive the shaft. The rotation knob defines an internal cavity in communication with the lumen that is configured to receive the bushing therein. The rotation knob includes a plurality of radially-spaced fingers extending proximally from a proximal end thereof. The fingers each include a radially outwardly-extending tab disposed at a free end thereof. The tabs cooperating to define an outer peripheral diameter. The rotation knob is transitionable between a first at-rest position and a first flexed position, while the fingers are transitionable between a second at-rest position and a second flexed position. In the first flexed position, the rotation knob is flexed to expand a diameter of the lumen to permit passage of the bushing distally through the lumen and into the internal cavity of the rotation knob. In the first at-rest position, the diameter of the lumen generally approximates a diameter of the shaft to engage the bushing within the internal cavity. In the second flexed position, the fingers are flexed radially-inwardly such that the fingers are permitted to pass through the aperture defined within the distal surface of the housing. In the second at-rest position, the outer peripheral diameter defined by the tabs of the fingers is greater than a diameter of the aperture defined through the distal surface of the housing to rotatably engage the distal surface of the housing within a slot defined between the proximal end of the rotation knob and the tabs of the fingers, with the shaft extending through the lumen of the rotation knob.

In one aspect, the fingers are biased towards the second at-rest position.

In another aspect, the rotation knob is biased towards the first at-rest position.

In still another aspect, the rotation knob includes a plurality of alternating flanges and recesses disposed on the outer periphery thereof. The alternating flanges and recesses are configured to facilitate grasping and rotating the rotation knob.

In yet another aspect, the rotation knob and fingers are monolithically formed as a single component.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
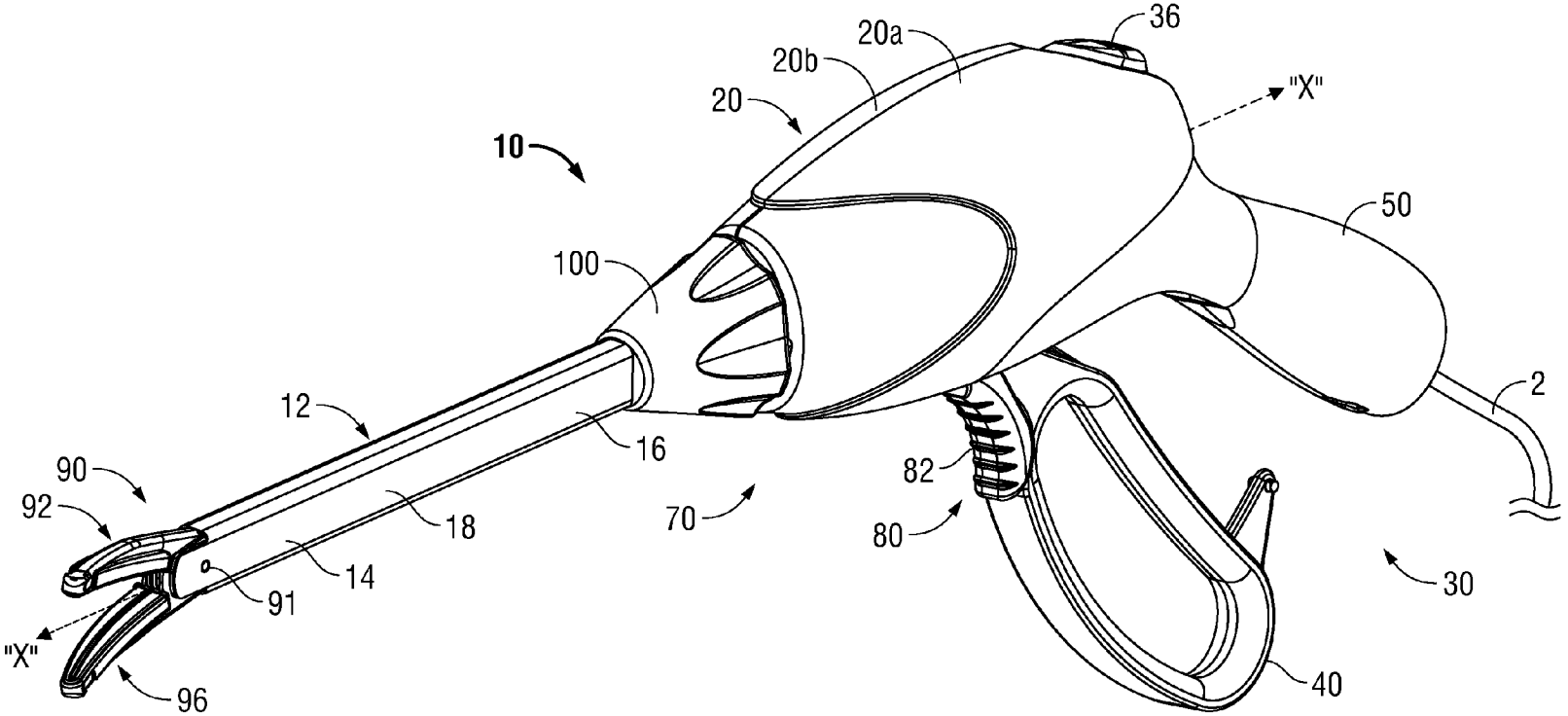
FIG. 1 is a perspective view of an endoscopic surgical forceps configured for use in accordance with the present disclosure.
Figure 2:
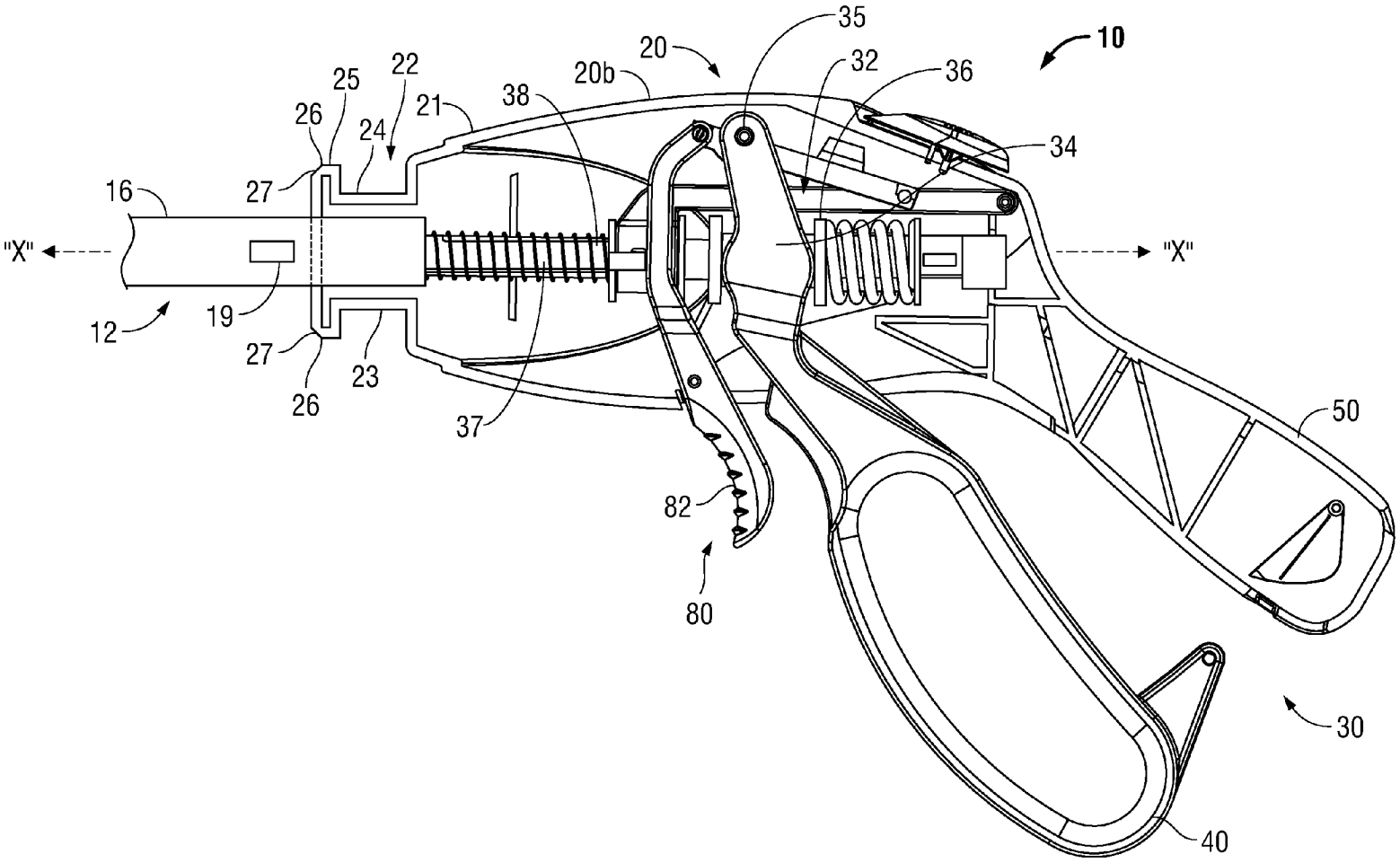
FIG. 2 is a side, cut-away view of a housing of the forceps of FIG. 1.
Figure 3:
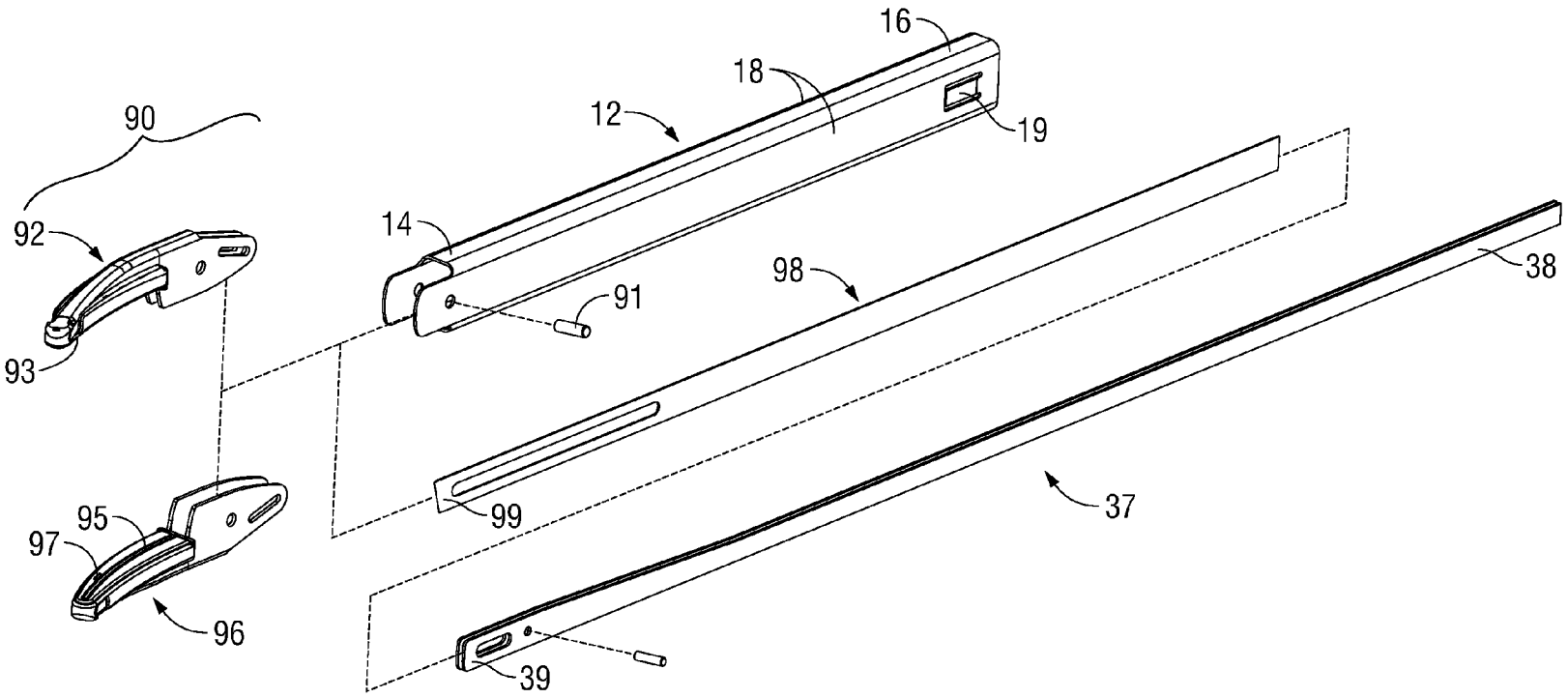
FIG. 3 is an perspective view of a shaft and an end effector assembly of the forceps of FIG. 1 shown with parts separated.

FIGS. 1-3 show in detail the operating features and inter-cooperating components of one example of a surgical instrument, forceps 10, configured for use in accordance with the present disclosure. Although the present disclosure is described with exemplary reference to forceps 10, the present disclosure is equally applicable for use with any other suitable surgical instrument having a housing including one or more mechanical and/or electrical controls operable to control and/or manipulate an end effector assembly of the surgical instrument. For the purposes herein, forceps 10 is generally described.

Forceps 10 defines a longitudinal axis "X-X" and includes a housing 20, a handle assembly 30, a rotating assembly 70, a trigger assembly 80 and an end effector assembly 90. Forceps 10 further includes a shaft 12 having a distal end 14 configured to mechanically engage end effector assembly 90 and a proximal end 16 that mechanically engages housing 20. Forceps 10 also includes cable 2 that connects forceps 10 to a generator (not shown) or other suitable power source, although forceps 10 may alternatively be configured as a battery powered instrument. Cable 2 includes wires (not shown) extending therethrough that have sufficient length to extend through shaft 12 in order to provide energy to at least one of the jaw members 92 and 96 of end effector assembly 90.

With continued reference to FIGS. 1-3, handle assembly 30 includes a fixed handle 50 and a movable handle 40. Fixed handle 50 is integrally associated with housing 20 and handle 40 is movable relative to fixed handle 50. Rotating assembly 70, as will be described in greater detail below, includes a rotation knob 100 that is rotatable in either direction about longitudinal axis "X-X" to rotate end effector assembly 90 about longitudinal axis "X-X."

End effector assembly 90 is shown attached at a distal end 14 of shaft 12 and includes a pair of opposing jaw members 92 and 96. More specifically, jaw members 92, 96 are pivotably coupled to shaft 12 via pivot 91. Each jaw member 92, 96 includes an opposed, electrically conductive tissue sealing surface 93, 97, respectively. End effector assembly 90 is configured as a bilateral assembly, i.e., where both jaw member 92 and jaw member 96 are movable about pivot 91 relative to one another and to shaft 12. However, end effector assembly 90 may alternatively be configured as a unilateral assembly, i.e., where one of the jaw members 92, 96 is fixed relative to shaft 12 and the other jaw member 92, 96 is movable about pivot 91 relative to shaft 12 and the fixed jaw member 92, 96. A knife assembly 98 is disposed within shaft 12 and a knife channel 95 is defined within one or both jaw members 92, 96 to permit reciprocation of a knife blade 99 therethrough, e.g., via activation of trigger 82 of trigger assembly 80, to cut tissue grasped between jaw members 92, 96.

Continuing with reference to FIGS. 1-3, housing 20 houses the internal working components of forceps 10 and is formed from first and second cooperating housing parts 20a, 20b. Housing halves 20a, 20b may be snap-fit, or otherwise engaged to one another to form housing 20. Movable handle 40 of handle assembly 30 extends into housing 20, ultimately connecting to a drive assembly 32 that, together, mechanically cooperate to impart movement of jaw members 92 and 96 between a spaced-apart position and an approximated position to grasp tissue between sealing surfaces 93, 97 of jaw members 92, 96, respectively. More specifically, movable handle 40 includes a pair of driving flanges 34 that extends upwardly into housing 20 on either side of drive assembly 32, ultimately pivotably coupling to housing 20 via pivot 35. Driving flanges 34 are received within mandrel 36 of drive assembly 32, which is disposed about proximal end 38 of drive bar 37, while jaw members 92, 96 are pivotably coupled to distal end 39 of drive bar 37. Due to this configuration, upon pivoting of movable handle 40 relative to fixed handle 50, driving flanges 34 are pivoted about pivot 35, thereby urging mandrel 36 and drive bar 37 to translate longitudinally along longitudinal axis "X-X" and through shaft 12 to pivot jaw members 92, 96 between the spaced-apart and approximated positions. As shown in FIG. 1, movable handle 40 is initially spaced-apart from fixed handle 50 and, correspondingly, jaw members 92, 96 are in the spaced-apart position. Movable handle 40 is depressible from this initial position to a depressed position corresponding to the approximated position of jaw members 92, 96.

Figure 5A:
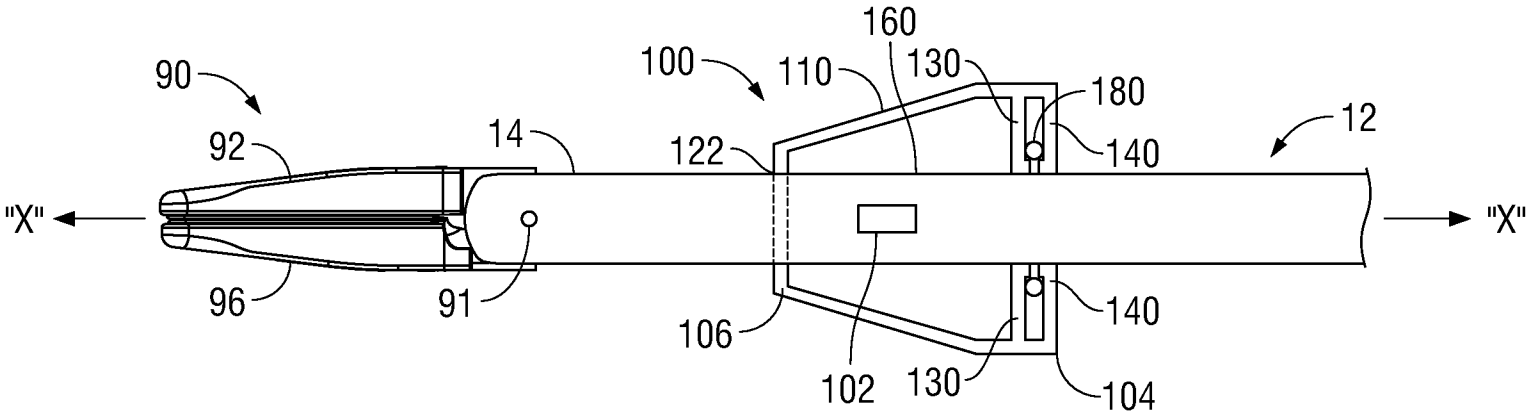
FIG. 5A is a side view of a distal end of the shaft of the forceps of FIG. 1 showing the rotation knob of FIG. 4A sliding proximally therealong.
Figure 5B:
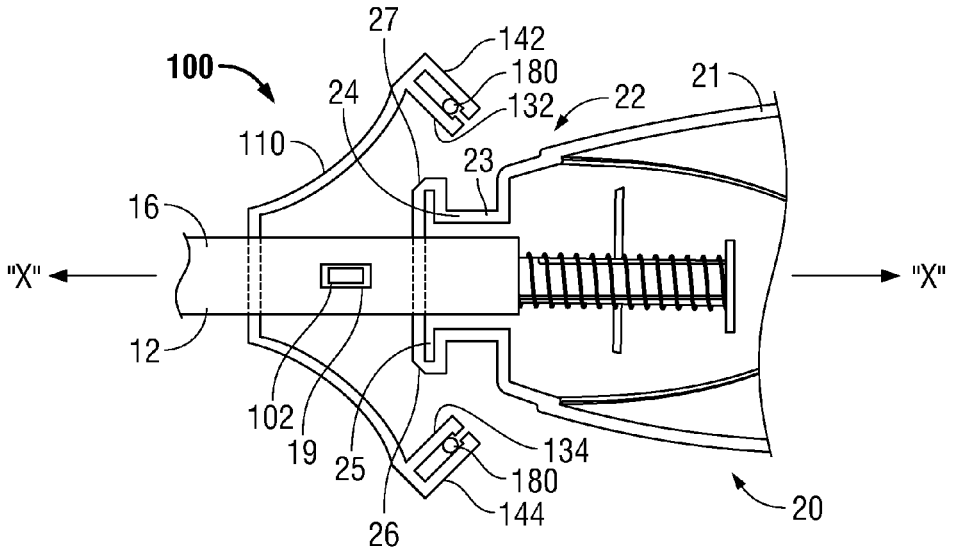
FIG. 5B is a side, cut-away view of a distal end of the housing of FIG. 2 showing the rotation knob of FIG. 4A flexed outwardly for engagement about the housing.
Figure 5C:
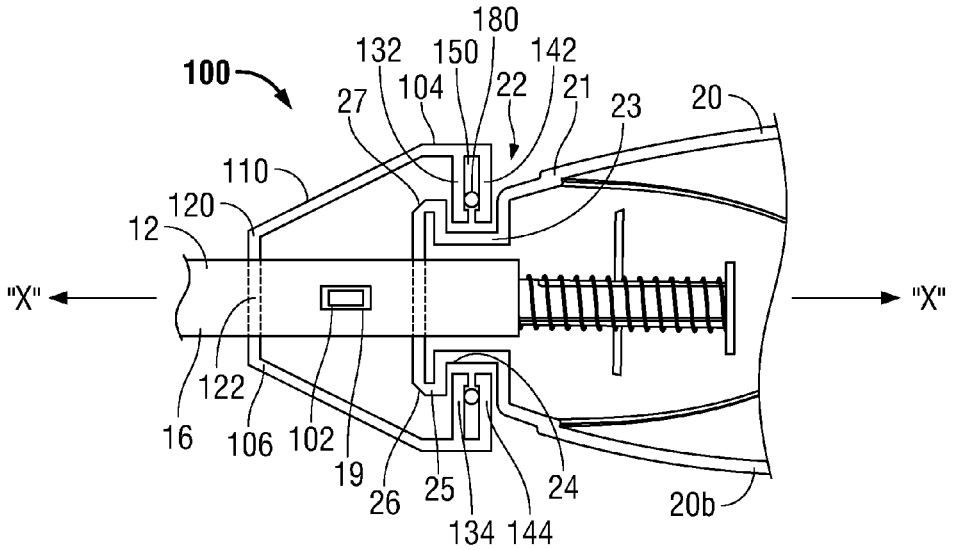
FIG. 5C is a side, cut-away view of a distal end of the housing of FIG. 2 shown including the rotation knob of FIG. 4A engaged thereon.

With continued reference to FIGS. 1-3, in conjunction with FIG. 5C, rotation knob 100 is disposed about both proximal end 16 of shaft 12 and nose 22 of housing 20 and, as mentioned above, is rotatable in either direction about longitudinal axis "X-X" to rotate end effector 100 about longitudinal axis "X-X." Shaft 12 includes a pair of cut-outs 19 defined within opposed sides 18 thereof at proximal end 16 of shaft 12 and rotation knob 100 includes a pair of protrusions 102 shaped complementarily to cut-outs 19 such that, upon positioning of rotation knob 100 about proximal end 16 of shaft 12, protrusions 102 are received within cut-outs 19 to engage rotation knob 100 and shaft 12 to one another. With rotation knob 100 and shaft 12 engaged to one another, rotation knob 100 may be rotated about longitudinal axis "X-X" to effect corresponding rotation of shaft 12 and end effector assembly 90 about longitudinal axis "X-X."

Nose 22 of housing 20 is configured to accept proximal end 104 of rotation knob 100 thereon to permit rotatable coupling of rotation knob 100 and housing 20 to one another. Nose 22 of housing 20 includes a neck 23 extending distally from body portion 21 of housing 20 and a distal base 25 disposed at free end 24 of neck 23. Neck 23 defines a reduced diameter as compared to distal base 25 of nose 22 such that, as will be described below, when proximal end 104 of rotation knob 100 is disposed about neck 23, rotation knob 100 is retained in fixed longitudinal position relative to nose 22 between body portion 21 of housing 20 and distal base 25 of nose 22. The specific features and configuration of rotation knob 100 and other embodiments of rotation knobs configured for use with forceps 10 are described in greater detail below.

Turning now to FIGS. 4A-4E and 5A-5C, rotation knob 100 defines a generally conically-shaped configuration having a minimum diameter at distal end 106 thereof and a maximum diameter at proximal end 104 thereof, although other configurations are also contemplated. Rotation knob 100 includes a shell 110 defining the conically-shaped configuration of rotation knob 100 and includes a generally hollow interior 112, a distal wall 120 defining distal end 106 of rotation knob 100, and first and second sets of proximal support walls 130, 140 defining proximal end 104 of rotation knob 100. Distal wall 120 defines an aperture 122 therethrough that generally approximates the dimensions of shaft 12 such that shaft 12 is permitted to pass therethrough. Walls 132, 134 of the first set of proximal support walls 130 extend inwardly from opposed sides of shell 110 and each define opposed surface 133, 135, respectively. Surfaces 133, 135 may define curvate configurations (or any other suitable configurations) that cooperate to define an aperture 136 therebetween that is substantially aligned with aperture 122 defined through distal wall 120. Aperture 136, in its at-rest position, generally approximates the dimensions of neck 23 of nose 22, such that proximal end 104 of rotation knob 100 may be disposed about nose 22 of housing 20, as will be described in greater detail below. Walls 142, 144 of the second set of proximal support walls 140 are spaced-apart from walls 132, 134 of the first set of proximal support walls 130 to define an annular slot 150 therebetween. Walls 142, 144 of the second set of proximal support walls 140, similar to the first set of proximal support walls 130, extend inwardly from opposed sides of shell 110 and each define an opposed surface 143, 145, respectively, e.g., a curvate surface (although other configurations are contemplated), that cooperate to define an aperture 146 that is substantially aligned with apertures 122 and 136. Similar to aperture 136, aperture 146, in its at-rest position, generally approximates the dimensions of neck 23 of nose 22, such that proximal end 104 of rotation knob 100 may be rotatably engaged about nose 22 of housing 20, as will be described in greater detail below. Apertures 122, 136, 146 together cooperate to define a lumen 160 extending longitudinally though rotation knob 100. Lumen 160 is configured to receive shaft 12 therethrough, thus permitting rotation knob 100 to be disposed about shaft 12 in a substantially at-rest position, as will be described below.

With continued reference to FIGS. 4A-4E and 5A-5C, rotation knob 100 includes a plurality of alternating flanges 114 and recesses 116 annularly disposed about the outer periphery of shell 110 towards proximal end 104 of rotation knob 100 (although other configurations are contemplated) to facilitate grasping and rotating rotation knob 100. Rotation knob 100 is monolithically formed as a single component and may be formed from any suitable material, e.g., biocompatible polymer(s), that provides at least some degree of flexibility to permit engagement of rotation knob 100 about nose 22 of housing 20, as will be described below. Further, shell 110 may be formed from a relatively thin material to facilitate flexing of shell 110 for engaging (and disengaging) rotation knob 100 about nose 22 of housing 20, while distal wall 120 and the sets of proximal support walls 130, 140 provide strength and support to rotation knob 100. Rotation knob 100 may also include a plurality of cut-outs 118 defined annularly about shell 110 at proximal end 104 thereof to provided increase flexibility to shell 110, e.g., to facilitate the outward-flexing of proximal end 104 of shell 110 such that shell 110 may be positioned about nose 22.

Continuing with reference to FIGS. 4A-4E and 5A-5C, shell 110 includes a pair of opposed protrusions 102 extending inwardly into hollow interior 112 of shell 110 that are configured to engage opposed cut-outs 19 defined within shaft 12 to engage rotation knob 100 and shaft 12 to one another. Protrusions 102 extend into lumen 160 defined through rotation knob 100 and are longitudinally disposed between distal wall 120 of rotation knob 100 and first set of proximal support walls 130 of rotation knob 100. Rotation knob 100 further includes a retaining ring 180 housed within annular slot 150 defined between the sets of proximal support walls 130, 140. Retaining ring 180 is secured within annular slot 150 via flanges 137, 139 of walls 132, 134 and flanges 147, 149 of walls 147, 149, although retaining ring 180 may otherwise be secured within annular slot 150 in any suitable fashion, e.g., mechanical engagement, friction-fitting, adhesion, etc.

Figure 4A:
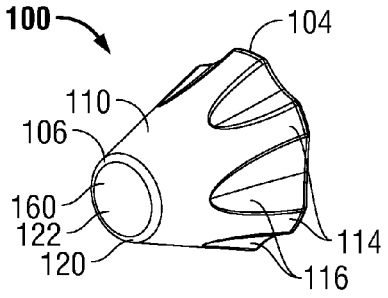
FIG. 4A is a perspective view of one embodiment of a rotation knob configured for use with the forceps of FIG. 1.
Figure 4B:
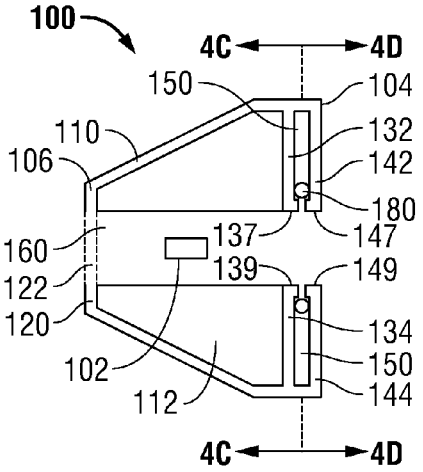
FIG. 4B is a longitudinal, cross-sectional view of the rotation knob of FIG. 4A.
Figure 4C:
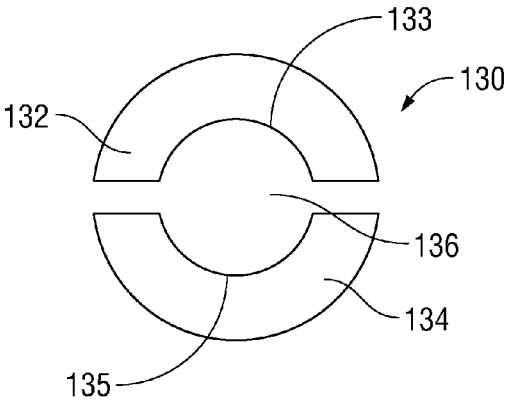
FIG. 4C is a transverse, cross-sectional view taken along section line 4C-4C of FIG. 4B.
Figure 4D:
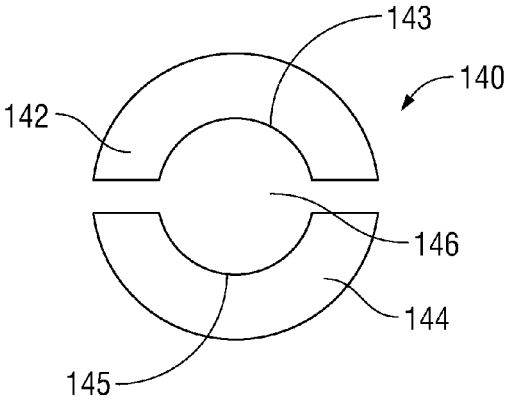
FIG. 4D is a transverse, cross-sectional view taken along section line 4D-4D of FIG. 4B.
Figure 4E:
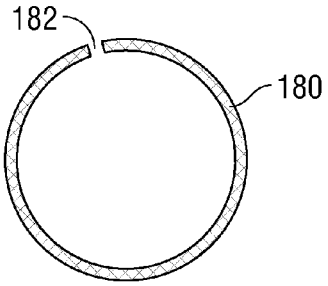
FIG. 4E is a top view of a retaining ring of the rotation knob of FIG. 4A.

As best shown in FIG. 4E, retaining ring 180 is formed from wire in a substantially ring-shaped configuration defining an interruption 182 that provides resilient flexibility to retaining ring 180, e.g., to permit radial expansion and contraction of ring 180. The wire forming retaining ring 180 may define a circular, oval, square, star-shaped, or any other suitable cross-sectional configuration. Alternatively, retaining ring 180 may be formed from any other suitable resiliently flexible material and/or may define any other suitable configuration that provides resilient flexibility to retaining ring 180. As will be described below, the resiliently flexible configuration of retaining ring 180 biases retaining ring towards an at-rest or contracted condition that, in turn, biases rotation knob 100 towards an at-rest, or un-flexed position (see FIG. 5C).

Turning now to FIGS. 5A-5C, in conjunction with FIGS. 1 and 4A-4E, the assembly of rotation knob 100 on a surgical instrument, e.g., forceps 10, and the use of rotation knob 100 in conjunction with forceps 10 to effect rotation of end effector assembly 90 is described. As will become apparent in view of the following, the configuration of rotation knob 100 permits efficient assembly and disassembly of rotation knob 100 on forceps 10 without requiring additional tools for assembly, without requiring multiple components cooperating to form rotation knob 100, and without compromising the integrity of rotation knob 100.

Initially, as shown in FIG. 5A, in conjunction with FIGS. 4A-4E, rotation knob 100 is slid proximally over end effector assembly 90 with end effector assembly 90 passing through lumen 160 defined through shell 110 of rotation knob 100. As mentioned above, lumen 160 is configured to receive shaft 12 therethrough such that rotation knob 100 may be easily slid proximally along shaft 12 towards housing 20. Lumen 160 is configured to permit passage of shaft 12 therethrough without requiring substantial flexing of rotation knob 100 such that, at this point, shell 110 and retaining ring 180 of rotation knob 100 remain disposed in their respective at-rest positions (the at-rest position of rotation knob 100). Upon reaching proximal end 16 of shaft 12, with rotation knob 100 disposed in the at-rest position, rotation knob 100 is inhibited from being translated further proximally due to the abutment of the second set of proximal support walls 140 of rotation knob 100 and distal base 25 of nose 22 of housing 20. That is, distal base 25 of nose 22 of housing 20 defines a diameter larger than the at-rest diameter of lumen 160 of shell 110 of rotation knob 100 such that distal base 25 is inhibited from passing through lumen 160 when rotation knob 100 is disposed in the at-rest position. Thus, in order to permit passage of proximal end 104 of rotation knob 100 proximally beyond distal base 25 of nose 22 and into position about neck 23 of nose 22, rotation knob 100 is must flex from the at-rest position to a flexed position, thereby increasing the diameter of lumen 160 so as to permit 25 passage of distal base 25 of nose 22 therethrough.

As shown in FIG. 5B, in conjunction with FIGS. 4A-4E, in order to permit passage of rotation knob 100 over distal base 25 of nose 22, proximal end 104 of rotation knob 100 is flexed radially outwardly to expand lumen 160 to a sufficient diameter to permit passage of distal base 25 therethrough. That is, proximal end 104 of shell 110 is flexed radially outwardly such that walls 132, 134 of the first set of proximal support walls 130 are moved apart from one another and such that walls 142, 144 of the second set of proximal support walls 140 are likewise moved apart from one another to increase the diameter of apertures 136, 146, respectively, and, thus, the portion of lumen 160 extending through proximal end 104 of rotation knob 100. Upon outward flexing of proximal end 104 of shell 110, retaining ring 180 is likewise expanded against its bias to permit expansion of apertures 136, 146. Further, distal outer corner 26 of distal base 25 of nose 22 may define an angled surface 27 to facilitate outward flexing of shell 110 of rotation knob 100 as rotation knob 100 is urged proximally about distal base 25 of nose 22, e.g., angled surface 27 of distal base 25 permits proximal end 104 of rotation knob 100 to cam therealong towards the flexed position.

Rotation knob 100, in this flexed position, is advanced further proximally until the first and second sets of proximal support walls 130, 140, respectively, of rotation knob 100 are disposed proximally of distal base 25 of nose 22 and are positioned adjacent to neck 23 of nose 22. In this position, as shown in FIG. 5C, distal base 25 of nose 22 is disposed within hollow interior 112 of shell 110 longitudinally between distal wall 120 and the first set of proximal support walls 130. Upon achieving this position, with distal base 25 no longer disposed between the opposed walls 132, 134 and 142, 144 of first and second sets of proximal support walls 130, 140, respectively, and under the bias of retaining ring 180 and shell 110, proximal end 104 of rotation knob 100 is returned back towards the at-rest position (wherein apertures 136, 146 are returned towards their at-rest diameters) such that walls 132, 134 and 142, 144 are approximated, or clamped about neck 23 of nose 22. In this position, proximal end 104 of rotation knob 100 is engaged about nose 22 of housing 20, i.e., neck 23 of nose 22 extends through apertures 136, 146 defined by first and second sets of proximal support walls 130, 140, respectively, while distal end 106 of rotation knob 100 is disposed about proximal end 16 of shaft 12, i.e., proximal end 16 of shaft 12 extends through aperture 122 defined through distal wall 120 of rotation knob 100.

With continued reference to FIG. 5C, in conjunction with FIGS. 4A-4E, rotation knob 100 is retained in substantially fixed longitudinal position relative to nose 22 due to the positioning of the first and second sets of proximal support walls 130, 140, respectively, between body portion 21 of housing 20 and distal base 25 of nose 22 and under the bias of retaining ring 180 and shell 110. However, although rotation knob 100 is substantially fixed in longitudinal position relative to nose 22 due to the engagement of proximal end 104 of rotation knob 100 about neck 23 of nose 22, rotation knob 100 is permitted to rotate about longitudinal axis "X-X" relative to housing 20. The bias of retaining ring 180 and shell 110 towards their respective at-rest positions, which bias first and second sets of proximal support walls 130, 140, respectively, to approximate, or clamp about neck 23 of nose 22 also helps maintain the engagement of housing parts 20a, 20b, to one another, i.e., the clamping of rotation knob 100 about nose 22 inhibits substantial separation of housing parts 20a, 20b from one another.

In the engaged position, wherein rotation knob 100 is engaged about nose 22, protrusions 102 of rotation knob 100, which extend inwardly into hollow interior 112 of shell 110, are biased into engagement within cut-outs 19 defined within shaft 12 to rotatably fix rotation knob 100 and shaft 12 to one another. Thus, upon rotation of rotation knob 100 relative to housing 20, shaft 12 and end effector assembly 90 are similarly rotated relative to housing 20. Further, the bias of retaining ring 180 to clamp proximal end 104 of rotation knob 100 about neck 23 of nose 22 may be sufficient to retain rotation knob 100 and, thus, end effector assembly 90 in fixed rotational orientation in the absence of manipulation of rotation knob 100. Alternatively, neck 23 of nose 22 may includes a plurality of notches (not explicitly shown) defined therein that correspond to pre-determined intervals of rotation, e.g., 30 degrees, 60 degrees, 90 degrees, etc., of end effector assembly 90. As such, rotation knob 100 may be incrementally rotated and locked in engagement with each successive notch (not shown) under the bias of retaining ring 180 and shell 110 to rotate and fix end effector assembly 90 in various different rotational positions.

Referring again to FIGS. 4A-4E and 5A-5C, in order to disengaged rotation knob 100 from nose 22 of housing 20 and shaft 12, proximal end 104 of shell 110 of rotation knob 100 is flexed radially outwardly to the flexed position such that walls 132, 134 of the first set of proximal support walls 130 are moved apart from one another and such that walls 142, 144 of the second set of proximal support walls 140 are moved apart from one another to expand retaining ring 180, thus permitting expansion of apertures 136, 146. Apertures 136, 146, are expanded sufficiently so as to permit passage of proximal end 104 of rotation knob 100 distally over distal base 25 of nose 22 of housing 20 to disengage rotation knob 100 from housing 20. Further, upon outward flexing of shell 110, protrusions 102 are withdrawn from cut-outs 19 defined within shaft 12 to disengage shaft 12 and rotation knob 100 from one another. Once rotation knob 100 has been disengaged from shaft 12 and nose 22, rotation knob 100 may be slid distally along shaft 12, ultimately passing over end effector assembly 90 to remove rotation knob 100 from forceps 10.

Figure 6:
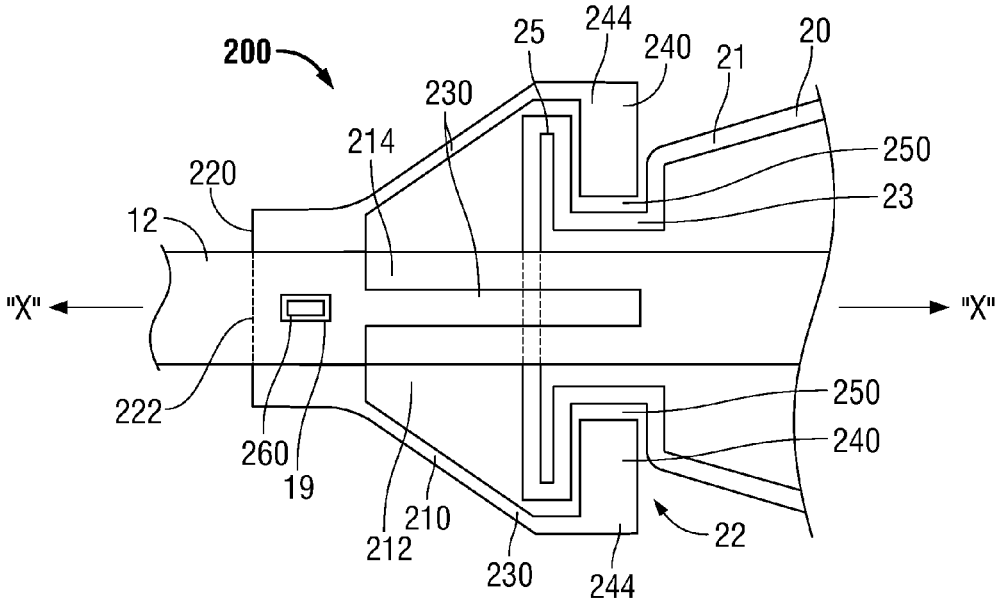
FIG. 6 is a side, cut-away view of a distal end of the housing of the forceps of FIG. 1 shown including another embodiment of a rotation knob engaged thereon.

Turning now to FIG. 6, another embodiment of a rotation knob 200 configured for use with forceps 10 is shown. Rotation knob 200 is similar to rotation knob 100 (FIGS. 4A-4E) and defines a generally conically-shaped configuration, although other configurations are also contemplated. Rotation knob 200 is monolithically formed as a single component and may be formed from any suitable material, e.g., biocompatible polymer(s), that provides at least some degree of flexibility to permit engagement of rotation knob 100 about nose 22 of housing 20. Rotation knob 200, except where specifically contradicted below, may include any of the features discussed above with respect to rotation knob 100 (FIGS. 4A-4E).

Continuing with reference to FIG. 6, rotation knob 200 includes a shell 210 defining the conically-shaped configuration of rotation knob 200 and having a generally hollow interior 212, a distal wall 220 defining distal end 202 of rotation knob 200, a plurality, e.g., four (4), spaced-apart, proximally-extending fingers 230 disposed at proximal end 204 of rotation knob 200, and a lumen 214 extending longitudinally through shell 210 of rotation knob 200. Shell 210 of rotation knob 200 includes a pair of opposed protrusions 260 extending inwardly into hollow interior 212 of shell 210 that are configured to engage opposed cut-outs 19 defined within shaft 12 to engage rotation knob 200 and shaft 12 to one another. Protrusions 260 extend into lumen 214 defined through rotation knob 200 and are longitudinally disposed between distal wall 220 and fingers 230 of rotation knob 200.

Each finger 230 of rotation knob 200 includes an inwardly-extending tab 240 disposed at a free end 244 thereof. Tabs 240 of fingers 230 cooperate to define an aperture 250 through proximal end 204 of rotation knob 200 that, in conjunction with aperture 250 defined through distal wall 220, define lumen 214 extending longitudinally through rotation knob 200. Fingers 230 are formed at least partially from a resiliently flexible material, thus permitting fingers 230 to flex radially outwardly from an at-rest position to a flexed position, wherein the diameter of aperture 250 is expanded to permit passage of proximal end 204 of rotation knob 200 about distal base 25 of nose 22 of housing 20. Fingers 230 are biased towards the at-rest position, wherein the diameter of aperture 250 generally approximates the diameter of shaft 12, thus permitting passage of shaft 12 therethrough while fingers 230 of rotation knob 200 remain in a substantially at-rest, or un-flexed position.

In use, rotation knob 200 is first slid proximally over end effector assembly 90 with end effector assembly 90 passing through lumen 214 defined through shell 210 of rotation knob 200. Upon reaching proximal end 16 of shaft 12, with rotation knob 200 still disposed in the at-rest position, rotation knob 200 is inhibited from being translated further proximally due to the abutment of tabs 240 of fingers 230 of rotation knob 200 and distal base 25 of nose 22 of housing 20. Thus, in order to permit passage of proximal end 204 of rotation knob 200 proximally beyond distal base 25 of nose 22 and into position about neck 23 of nose 22, fingers 230 are flexed radially outwardly from the at-rest position to the flexed position, thereby increasing the diameter of aperture 250 and, thus, the proximal portion of lumen 214 so as to permit passage of distal base 25 of nose 22 therethrough.

Rotation knob 200, in this flexed position, is now permitted to be advanced further proximally such that tabs 240 of fingers 230 are moved proximally over distal base 25 of nose 22 into position adjacent neck 23 of nose 22. In this position, as shown in FIG. 5C, distal base 25 of nose 22 is disposed within hollow interior 212 of shell 210 longitudinally between distal wall 220 and fingers 230. Upon achieving this position, with distal base 25 no longer disposed between fingers 230, fingers 230 are resiliently biased back towards the at-rest position such that tabs 240 are approximated about neck 23 of nose 22 and aperture 250 is returned towards its at-rest diameter. In this position, with tabs 240 approximated, or clamped about neck 23 of nose 22, rotation knob 200 is retained in substantially fixed longitudinal position relative to nose 22 due to the positioning of tabs 240 of fingers 230 between body portion 21 of housing 20 and distal base 25 of nose 22 under the bias of fingers 230, although rotation knob 200 is permitted to rotate about longitudinal axis "X-X" relative to housing 20. The clamping or bias of fingers 230 about neck 23 of nose 22 also helps maintain the engagement of housing parts 20a, 20b of housing 20 to one another, similarly as described about with respect to rotation knob 100 (see FIGS. 4A-4E).

In the engaged position, wherein rotation knob 200 is engaged about nose 22, protrusions 260 of rotation knob 200 are engaged within cut-outs 19 defined within shaft 12 to rotatably fix rotation knob 200 and shaft 12 to one another. Thus, upon rotation of rotation knob 200 relative to housing 20, shaft 12 and end effector assembly 90 are similarly rotated relative to housing 20.

In order to disengaged rotation knob 200 from nose 22 of housing 20 and shaft 12, fingers 230 are flexed radially outwardly from the at-rest position back to the flexed position to expand aperture 250 such that tabs 240 of fingers 230 may pass distally over distal base 25 of nose 22 of housing 20 to disengage rotation knob 200 from housing 20. Further, upon outward flexing of fingers 230, protrusions 260 are withdrawn from cut-outs 19 defined within shaft 12 to disengage shaft 12 and rotation knob 200 from one another. Once rotation knob 200 has been disengaged from shaft 12 and nose 22, rotation knob 200 may be slid distally along shaft 12, ultimately passing over end effector assembly 90 to remove rotation knob 200 from forceps 10.

Figure 7:
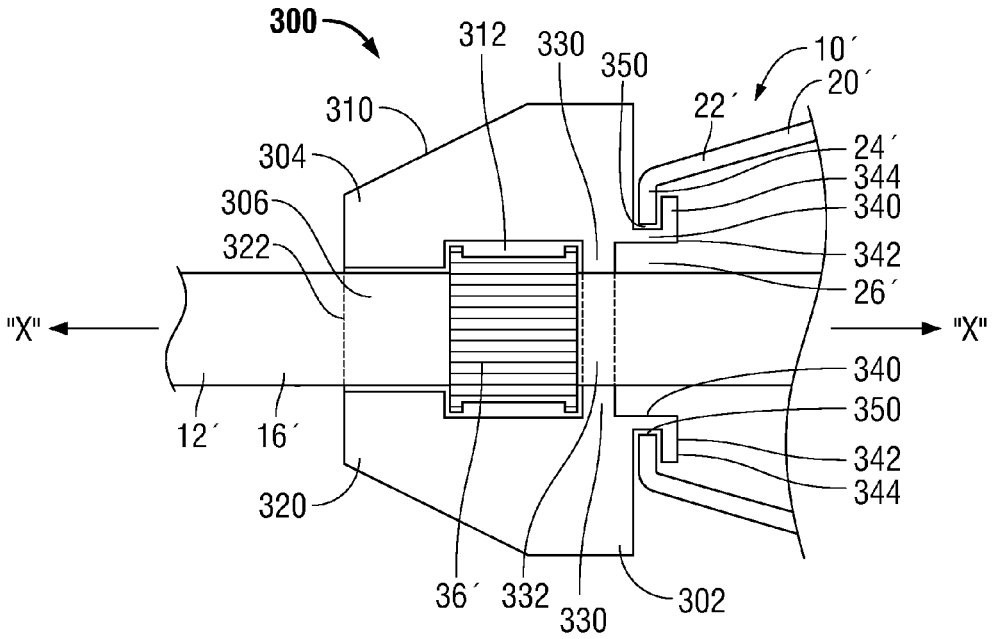
FIG. 7 is a side, cut-away view of a distal end of a housing of another embodiment of a forceps, shown including another embodiment of a rotation knob engaged thereon.

With reference to FIG. 7, another embodiment of a rotation knob 300 configured to engage a distal end 22' of a housing 20' of a surgical instrument 10' is shown. Surgical instrument 10' may be a forceps, e.g., a forceps similar to forceps 10 (FIG. 1), or any other suitable surgical instrument including an end effector assembly disposed at a distal end of a shaft and a housing at the proximal end of the shaft for controlling operation of the end effector assembly. Rotation knob 300 is configured for use with a surgical instrument 10' including a housing 20' having a distal surface 24' which defines a distal opening 26' therethrough, rather than a distal nose configuration such as that described above with respect to forceps 10 (FIG. 1). Further, rather than having cut-outs defined within the shaft, surgical instrument 10' includes a bushing 36' engaged about shaft 12' towards proximal end 16' thereof that is configured to be received within a cavity 312 defined within rotation knob 300 to secure rotation knob 300 and shaft 12' to one another such that rotation knob 300 can be rotated to effect similar rotation of shaft 12' and the end effector assembly (not shown) thereof. Rotation knob 300, except where specifically contradicted below, may include any of the features discussed above with respect to rotation knob 100 (FIGS. 4A-4E).

Continuing with reference to FIG. 7, rotation knob 300 includes a housing 310 defining a proximal end 302, a distal end 304, and a lumen 306 extending longitudinally therethrough. Lumen 306 is dimensioned to receive shaft 12' of surgical instrument 10' therethrough. More specifically, housing 310 includes a distal hub 320 disposed at distal end 304 thereof that defines an aperture 322 therethrough and a pair of opposed proximal walls 330 that cooperate to define an aperture 332 therethrough. Apertures 322, 332 cooperate with one another to define lumen 306 extending longitudinally through housing 310 of rotation knob 300. Housing 310 is at least partially formed from a resiliently flexible material that is transitionable between a first at-rest position and a first flexed position to permit proximal walls 330 to be flexed apart from one another, thereby increasing the diameter of aperture 332 and, thus, increasing the diameter of the proximal portion of lumen 306. Housing 310 also defines an internal cavity 312 disposed about lumen 306 that, as mentioned above, is configured to retain bushing 36' of surgical instrument 10' therein.

A plurality of spaced-apart fingers 340 extends proximally from proximal end 302 of housing 310. Each finger 340 includes an outwardly-extending flange 344 disposed at the free end 342 thereof. As a result of this configuration, a slot 350 is defined between flanges 344 of fingers 340 and proximal end 302 of housing 310. Fingers 340 are formed at least partially from a resiliently flexible material such that fingers 340 may be flexed radially-inwardly from a second at-rest position, wherein fingers 340 cooperate to define a first outer peripheral diameter, to a second flexed position, wherein fingers 340 converge towards one another to define a reduced outer peripheral diameter. Rotation knob 300, including fingers 340, may be monolithically formed as a single component.

In use, rotation knob 300 is first slid over the end effector assembly (not shown) of the surgical instrument 10' and proximally along shaft 12'. Upon reaching bushing 36', proximal end 302 of rotation knob 300 is flexed radially-outwardly from its at-rest position (e.g., the first at-rest position) to its flexed position (e.g., the first flexed position) to permit passage of bushing 36' through lumen 306 and into cavity 312 defined within housing 310. Bushing 36' is configured to be engaged within housing 310 via friction-fitting (under the resilient bias of housing 310 back to its at-rest position), or other suitable engagement, to engage shaft 12' and rotation knob 300 to one another such that rotation of rotation knob 300 relative to longitudinal axis "X-X" effects corresponding rotation of shaft 12' and the end effector assembly (not shown) about longitudinal axis "X-X." Once bushing 36' is positioned within cavity 312, housing 310 may be released to return under bias (or otherwise return) back towards the at-rest position to engage bushing 36' within cavity 312 of housing 310.

With housing 310 disposed about bushing 36' of shaft 12', rotation knob 300 may then be engaged to distal end 22' of housing 20'. In order to engage rotation knob 300 to distal end 22' of housing 20', fingers 340 are flexed inwardly from their at-rest position (e.g., the second at-rest position) to their flexed position (e.g., the second flexed position) to define a reduced outer peripheral diameter that is sufficiently small so as to permit passage of fingers 340 through distal opening 26' formed in distal surface 24' of housing 310. Upon passing through opening 26', fingers 340 are permitted to resiliently return back towards their at-rest position, thus engaging distal surface 24' of housing 20' within slot 350 defined between flanges 344 of fingers 340 and proximal end 304 of housing 310. In this engaged position, rotation knob 300 is substantially fixed in longitudinally position relative to housing 20', but is permitted to rotate about longitudinal axis "X-X" relative to housing 20'.

Disengagement of rotation knob 300 from housing 20' and shaft 12' is effected in the opposite manner as the engagement described above, namely, fingers 340 are flexed inwardly to the second flexed position wherein fingers 340 define a reduced outer peripheral diameter, thus permitting withdrawal of fingers 340 through distal opening 26' formed in distal surface 24' of housing 20'. Fingers 340 are then returned under bias back towards the second at-rest position. Thereafter, housing 310 of rotation knob 300 is flexed outwardly to the first flexed position to permit bushing 36' to be translated proximally through the expanded proximal portion of lumen 306 to remove bushing 36' from cavity 312 of rotation knob 300. Once bushing 36' has been removed from rotation knob 300, housing 310 is permitted to return under bias back towards the first at-rest position. Ultimately, rotation knob 300 is slid distally along shaft 12' and passed over the end effector assembly (not shown) thereof to remove rotation knob 300 from surgical instrument 10'.

Figure 8A:
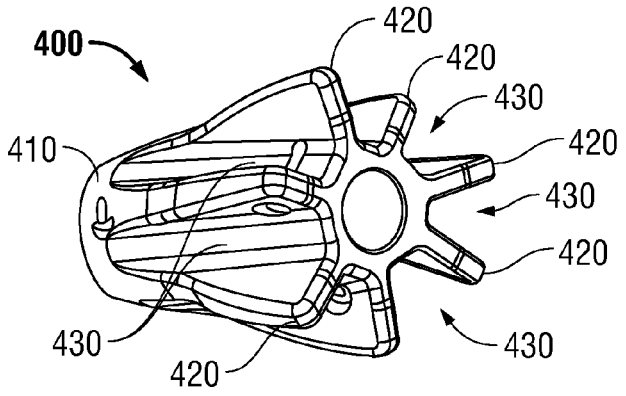
FIG. 8A is a perspective view of another embodiment of a rotation knob configured for use with the forceps of FIG. 1.
Figure 8B:
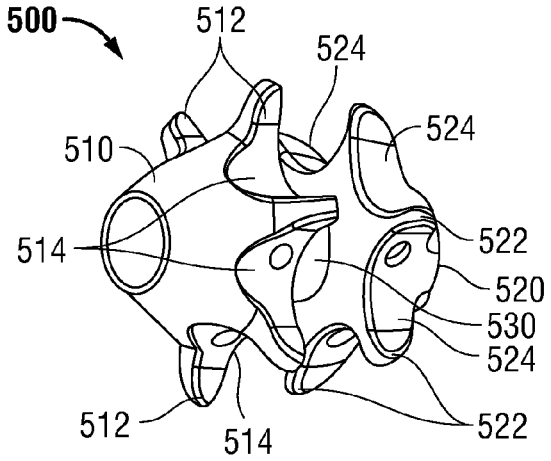
FIG. 8B is a perspective view of another embodiment of a rotation knob configured for use with the forceps of FIG. 1.
Figure 8C:
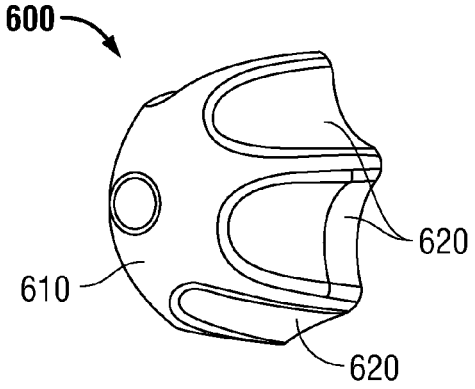
FIG. 8C is a perspective view of another embodiment of a rotation knob configured for use with the forceps of FIG. 1.

Referring now to FIGS. 8A-8C, various configurations of rotation knobs, e.g., rotation knobs 400, 500, 600, are shown. Rotation knobs 400, 500, 600 may be configured for use with forceps 10 (FIG. 1), surgical instrument 10' (FIG. 7), or any other suitable surgical instrument, similarly as described above with respect to rotation knobs 100, 200, 300 (FIGS. 5A-5C, 6, 7, respectively). Additionally, the ergonomic features of these rotation knobs, or any other suitable ergonomic features, may be incorporated into the rotation knobs described herein. In other words, although specific ergonomic features of rotation knobs 100-600 are shown and described herein, rotation knobs 100-600 may be provided in any suitable size, shape, and/or ergonomic configuration.

Further, it is envisioned that these various different rotation knobs be interchangeable with one another, thus allowing the user to select a desired rotation knob depending on the surgical procedure to be performed, the surgeon's preference, or other factors. This interchangeability is facilitated in that the rotation knobs described herein are easily and efficiently engaged and disengaged from a surgical instrument, e.g., forceps 10 (FIG. 1), thus allowing for easy and efficient interchanging of rotation knobs. This configuration provides increased customization and versatility to a surgical instrument, without requiring a separate instrument that is customized for each user and/or procedure. Such a configuration also permits the rotation knobs to be used as disposable components that can be easily engaged and disengaged from the reusable components of a particular surgical instrument, thus facilitating removal of the first, used rotation knob, sterilization of the reusable components, and reassembly of the instrument with a second, new rotation knob in preparation for reuse.

With reference to FIG. 8A, rotation knob 400 includes a generally-cylindrical body 410 having a plurality of flanges 420 extending radially outwardly therefrom substantially along the length of body 410. Flanges 420 taper distally to proximally and are spaced-apart from one another to define a plurality of finger recesses 430 therebetween that facilitate grasping and rotation of rotation knob 400. Rotation knob 400 may otherwise be configured similarly to any of the rotation knobs described above.

Referring to FIG. 8B, rotation knob 500 includes a pair of spaced-apart housing members 510, 520 interconnected by a tube segment 530. Housing members 510, 520 each define a generally annular configuration having a plurality of flanges 512, 522, respectively, extending radially outwardly therefrom. Flanges 512 are spaced-apart from one another, as are flanges 522, to define a plurality of finger recesses 514, 524, respectively, therebetween. Finger recesses 514, 524 facilitate the grasping and rotation of rotation knob 500. Rotation knob 500 may otherwise be configured similarly to any of the rotation knobs described above.

As shown in FIG. 8C, rotation knob 600 defines a more spherical-shaped body 610 and includes a plurality of fingertip-shaped recesses 620 defined therein for grasping and rotating rotation knob 600. Rotation knob 600 may otherwise be configured similarly to any of the rotation knobs described above.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:

a housing having a shaft extending distally therefrom and defining a longitudinal axis, the housing including a nose disposed at a distal end thereof, the nose including a neck extending distally from the housing and a base disposed at a distal end of the neck, the base defining a diameter greater than a diameter of the neck; and a rotation knob having a distal end defining a first aperture and a proximal end defining at least one second aperture, the first and second apertures cooperating to define a lumen extending longitudinally through the rotation knob that is configured to receive the shaft, the rotation knob flexible between an at-rest position and a flexed position, wherein, in the flexed position, the diameter of the second aperture is expanded from a first diameter to a second, larger diameter to permit passage of the base of the nose through the second aperture and into an interior of the rotation knob, and wherein, in the at-rest position, the second aperture defines the first diameter to rotatably engage the proximal end of the rotation knob about the nose with the shaft extending through the lumen of the rotation knob.

2. The surgical instrument according to claim 1, wherein the rotation knob includes at least one protrusion extending into the interior thereof, the at least one protrusion configured to engage the shaft to engage the rotation knob and the shaft to one another.

3. The surgical instrument according to claim 1, wherein the rotation knob includes a retaining ring configured to bias the rotation knob towards the at-rest position.

4. The surgical instrument according to claim 1, wherein the retaining ring includes an interruption defined therein to permit expansion of the retaining ring for transitioning the rotation knob between the at-rest and flexed positions.

5. The surgical instrument according to claim 3, wherein the rotation knob includes first and second pairs of proximal support walls, each pair of proximal support walls cooperating to define one of the at least one second apertures therethrough.

6. The surgical instrument according to claim 5, wherein the retaining ring is disposed between the first and second pairs of proximal support walls.

7. The surgical instrument according to claim 1, wherein the rotation knob includes a plurality of alternating flanges and recesses disposed on the outer periphery thereof, the alternating flanges and recesses configured to facilitate grasping and rotating the rotation knob.

8. The surgical instrument according to claim 1, wherein an outer distal corner of the base of the nose defines an angled surface configured to facilitate flexing of the rotation knob from the at-rest position to the flexed position to permit passage of the base through the second aperture.

9. The surgical instrument according to claim 1, wherein the rotation knob is monolithically formed as a single component.

10. The surgical instrument according to claim 1, wherein the housing is formed from first and second housing parts and wherein, when engaged about the nose of the housing, the rotation knob helps maintain the engagement of the first and second housing parts to one another.

11. A surgical instrument, comprising:

a housing having a shaft extending distally therefrom and defining a longitudinal axis, the housing including a nose disposed at a distal end thereof, the nose including a neck extending distally from the housing and a base disposed at a distal end of the neck, the base defining a diameter greater than a diameter of the neck; and a rotation knob having a distal end defining a first aperture and a plurality of radially-spaced fingers extending proximally from a proximal end of the rotation knob, the fingers each including a radially inwardly-extending tab disposed at a free end thereof, the tabs cooperating to define a second aperture, the first and second apertures cooperating to define a lumen extending longitudinally through the rotation knob that is configured to receive the shaft, the rotation knob flexible between an at-rest position and a flexed position, wherein, in the flexed position, the fingers are flexed radially outwardly to expand a diameter of the second aperture from a first diameter to a second, larger diameter, to permit passage of the base of the nose through the second aperture and into an interior of the rotation knob, and wherein, in the at-rest position, the second aperture defines the first diameter for rotatably engaging the tabs of the fingers of the rotation knob about the nose with the shaft extending through the lumen of the rotation knob.

12. The surgical instrument according to claim 11, wherein the rotation knob includes at least one protrusion extending into the interior thereof, the at least one protrusion configured to engage the shaft to engage the rotation knob and the shaft to one another.

13. The surgical instrument according to claim 11, wherein the fingers are biased towards the at-rest position.

14. The surgical instrument according to claim 11, wherein the rotation knob is monolithically formed as a single component.

15. The surgical instrument according to claim 11, wherein the housing is formed from first and second housing parts and wherein, when engaged about the nose of the housing, the rotation knob helps maintains the engagement of the first and second housing parts to one another.

*16. A surgical instrument, comprising:*

*a housing defining a nose at a distal end thereof;*

*a shaft defining a proximal end and a distal end, the proximal end of the shaft rotatably coupled to the housing, the shaft extending distally from the nose of the housing;*

*at least one first engagement feature disposed towards the proximal end of the shaft adjacent the nose of the housing;*

*an end effector assembly disposed at the distal end of the shaft and operably coupled to the shaft such that rotation of the shaft effects corresponding rotation of the end effector assembly; and*

*a monolithic rotation knob including a distal portion and a proximal portion, the monolithic rotation knob defining a lumen extending longitudinally therethrough configured to receive the shaft, the distal portion of the monolithic rotation knob including at least one second engagement feature disposed therein, the monolithic rotation knob configured to slide proximally about the shaft from a disengaged position to an engaged position, wherein, upon movement of the monolithic rotation knob from the disengaged position to the engaged position, the monolithic rotation knob is configured to flex from an at-rest position, wherein a portion of the lumen defines a first perimeter, to a flexed position, wherein the portion of the lumen defines a second, larger perimeter, and back to the at-rest position, and wherein, in the engaged position, the proximal portion of the monolithic rotation knob is disposed about the nose of the housing and the at least one second engagement feature is engaged with the at least one first engagement feature to engage the shaft and the monolithic rotation knob with one another such that rotation of the monolithic rotation knob about the nose of the housing rotates the shaft and the end effector assembly relative to the housing.*

*17. The surgical instrument according to claim 16, wherein the monolithic rotation knob includes a plurality of alternating flanges and recesses disposed on the outer periphery thereof, the alternating flanges and recesses configured to facilitate grasping and rotating the rotation knob.*

*18. The surgical instrument according to claim 16, wherein the at least one first engagement feature is a cut-out and wherein the at least one second engagement feature is a protrusion.*

* * * * *